United States Patent
Borali

(10) Patent No.: US 7,360,398 B2
(45) Date of Patent: Apr. 22, 2008

(54) RECEPTACLE FOR SENSORS

(75) Inventor: Stefano Borali, Mirandola (IT)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 11/466,678

(22) Filed: Aug. 23, 2006

(65) Prior Publication Data

US 2007/0039374 A1 Feb. 22, 2007

Related U.S. Application Data

(63) Continuation of application No. PCT/IT2004/000080, filed on Feb. 23, 2004.

(51) Int. Cl.
*G01N 7/00* (2006.01)
(52) U.S. Cl. ............................ 73/31.07; 128/205.23
(58) Field of Classification Search ............ 73/23.3, 73/431; 600/529
See application file for complete search history.

(56) References Cited

U.S. PATENT DOCUMENTS

| 4,679,573 A | * | 7/1987 | Parnoff et al. ............ 600/529 |
| 4,745,796 A | * | 5/1988 | Abdelrahman et al. .... 73/31.07 |
| 6,039,696 A | * | 3/2000 | Bell ........................ 600/532 |
| 6,895,803 B2 | * | 5/2005 | Seakins et al. ............ 73/29.02 |
| 2002/0078733 A1 | * | 6/2002 | Seakins et al. ............ 73/29.02 |
| 2006/0118113 A1 | * | 6/2006 | Bremner et al. ........ 128/204.22 |

FOREIGN PATENT DOCUMENTS

| EP | 1205747 A2 | 5/2002 |
| EP | 1329240 A1 | 7/2003 |
| WO | 8602820 | 5/1986 |
| WO | 2004039444 A1 | 5/2004 |

OTHER PUBLICATIONS

Written Opinion of the International Searching Authority, PCT/IT2004/000080, 5 pages, mailed Nov. 4, 2004.
International Search Report, PCT/IT2004/000080, 4 pages, mailed Nov. 4, 2004.
International Preliminary Report on Patentability, PCT/IT2004/000080, 11 pages, mailed Feb. 9, 2006.

* cited by examiner

*Primary Examiner*—Hezron Williams
*Assistant Examiner*—Samir M. Shah
(74) *Attorney, Agent, or Firm*—Baker Botts L.L.P.

(57) ABSTRACT

A receptacle for sensors insertable into a gas stream, houses at least one sensor for controlling at least one physical/chemical parameter of the gas stream, and is defined by at least one boundary wall, at least part of which is defined by a filtering element permeable solely to the gaseous phase of the gas stream.

6 Claims, 2 Drawing Sheets

RECEPTACLE FOR SENSORS

CROSS-REFERENCE TO RELATED APPLICATION

This application is a continuation of co-pending International Application No. PCT/IT2004/000080 filed Feb. 23, 2004, which designates the United States.

TECHNICAL FIELD

The present invention relates to a receptacle for sensors. More specifically, the present invention relates to a receptacle for sensors of a medical respiration support circuit, to which the following description refers purely by way of example.

BACKGROUND

In the medical equipment industry, a respiration support circuit is known comprising a conduit along which a stream of ventilation gas flows; and a cup-shaped receptacle extending at least partly inside the conduit to support a sensor, and designed to separate the sensor from the gas stream in the conduit, so that the sensor can be re-used for another patient without being cleaned, disinfected or sterilized.

Known medical respiration support circuits of the type described above have various drawbacks, mainly due to the receptacle only being designed to house temperature sensors, i.e., sensors whose operation does not depend on direct contact with the gas stream.

U.S. Pat. No. 4,745,796 discloses a receptacle insertable in a gas stream and housing at least one sensor for controlling at least one physical/chemical parameter of the gas stream. The receptacle comprises at least one boundary wall, which defines the receptacle itself, and which is defined at least partly by a filtering element permeable solely to the gaseous phase of the gas stream.

EP 1 205 747 A2 discloses a receptacle insertable in a gas stream and housing at least one sensor for controlling at least one physical/chemical parameter of the gas stream. The receptacle comprises at least one boundary wall, which defines the receptacle itself, and which is defined at least partly by a filtering element permeable solely to the gaseous phase of the gas stream.

SUMMARY

It is an object of the present invention to provide a receptacle for sensors, designed to eliminate the aforementioned drawbacks.

According to the present invention, there is provided a receptacle for sensors, the receptacle adapted for insertion into a gas stream. The receptacle is further adapted for housing at least one sensor for controlling at least one physical/chemical parameter of the gas stream. The receptacle comprises at least one boundary wall defining the receptacle. The boundary wall defines at least partly by a filtering element permeable solely to the gaseous phase of said gas stream.

According to the present invention, there is provided a receptacle for sensors, the receptacle adapted for insertion into a gas stream. The receptacle is further adapted for housing at least one sensor for controlling at least one physical/chemical parameter of the gas stream. The receptacle comprises at least one boundary wall defining the receptacle. The boundary wall is defined at least partly by a filtering element permeable solely to the gaseous phase of said gas stream.

BRIEF DESCRIPTION OF THE DRAWINGS

A non-limiting embodiment of the present invention will be described by way of example with reference to the accompanying drawings, in which.

DETAILED DESCRIPTION

Figure 1:
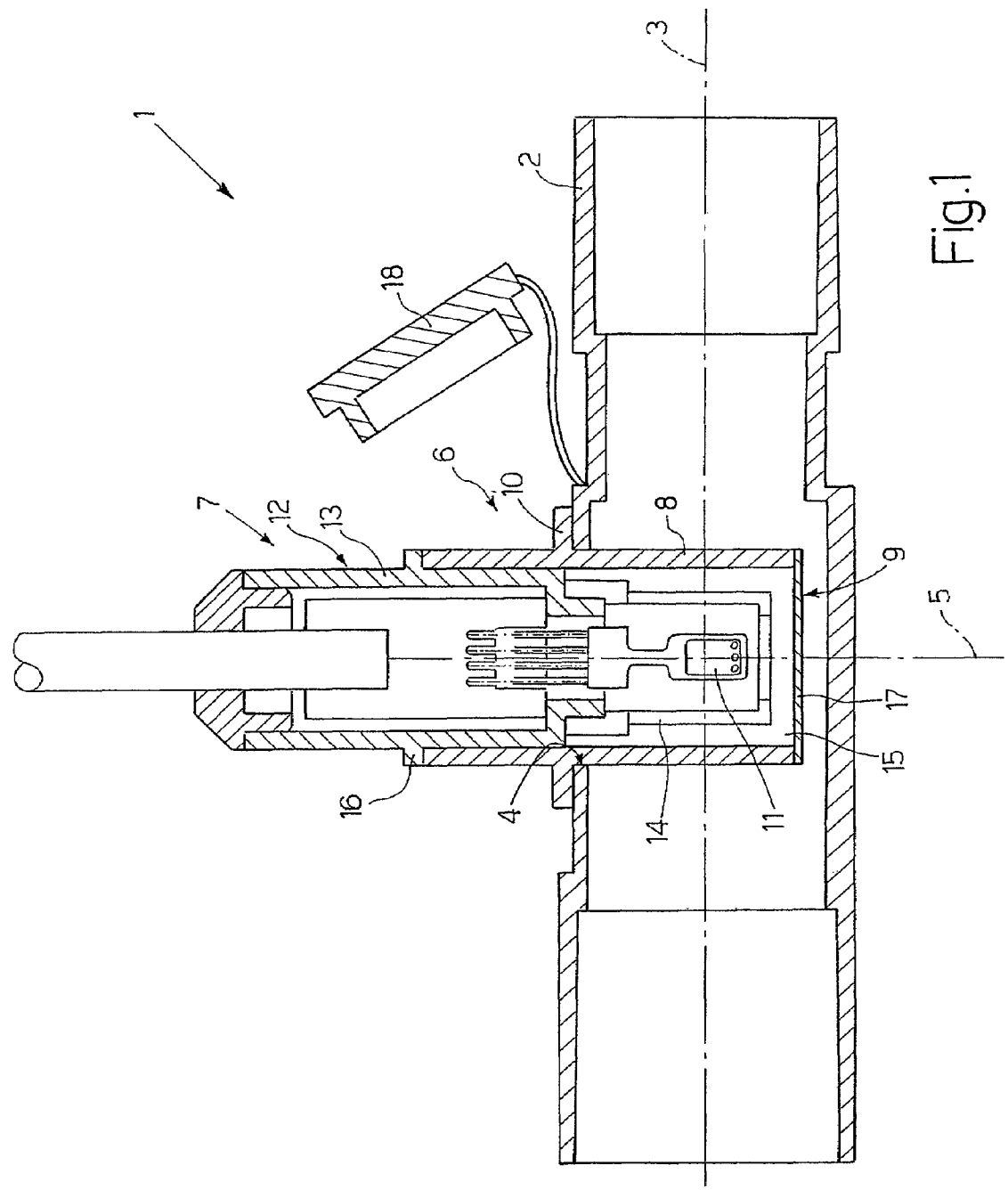
FIG. 1 shows a longitudinal section of a medical respiration support circuit conduit featuring a preferred embodiment of the receptacle for sensors according to the present invention.

Number 1 in FIG. 1 indicates as a whole a conduit of a medical respiration support circuit (not shown).

Conduit 1 comprises a tubular body 2, along which a stream of ventilation gas flows, and which has a given longitudinal axis 3, and a hole 4 formed radially through body 2 and having a longitudinal axis 5 crosswise to axis 3.

Conduit 1 also comprises a receptacle 6 for housing at least one sensor 7 controlling at least one physical/chemical parameter of the gas stream in body 2, and which extends inside body 2 through hole 4 and coaxially with axis 5.

Receptacle 6 is cup-shaped, is open outwards, is defined laterally by a substantially cylindrical wall 8 coaxial with axis 5, and is closed axially by a bottom wall 9 substantially perpendicular to wall 8 and to axis 5.

Wall 8 has an annular flange 10 substantially coaxial with axis 5, projecting radially outwards from the outer surface of wall 8, and which contacts body 2 when receptacle 6 is inserted axially inside hole 4; and wall 8 has an outside diameter approximately equal to but no smaller than the diameter of hole 4, so as to secure receptacle frictionally inside hole 4.

Sensor 7 comprises a sensitive element 11 inserted inside a tubular body 12, which is fitted inside receptacle 6, coaxially with axis 5, and comprises a wide portion 13, and a narrow portion 14 defined by a grill for protecting sensor 7, and which, together with receptacle 6, defines a chamber 15.

Portion 13 has an annular flange 16 substantially coaxial with axis 5, projecting radially outwards from the outer surface of portion 13, and which contacts wall 8 when body 12 is inserted axially inside receptacle 6; and portion 13 has an outside diameter approximately equal to but no smaller than the inside diameter of wall 8, so as to secure body 12 frictionally inside receptacle 6.

Wall 9 is defined by a permeable diaphragm 17, which permits the passage of gaseous phases, prevents the passage of solid and liquid phases, such as bacteria, viruses, water droplets, dust particles and/or biological fluids, and so only permits passage into chamber 15 of the gaseous phase of the gas stream in body 2, thus ensuring correct operation of sensor 7.

Receptacle 6 also has a cap 18, which is inserted into the free end of receptacle 6 in the absence of sensor 7.

Figure 2:
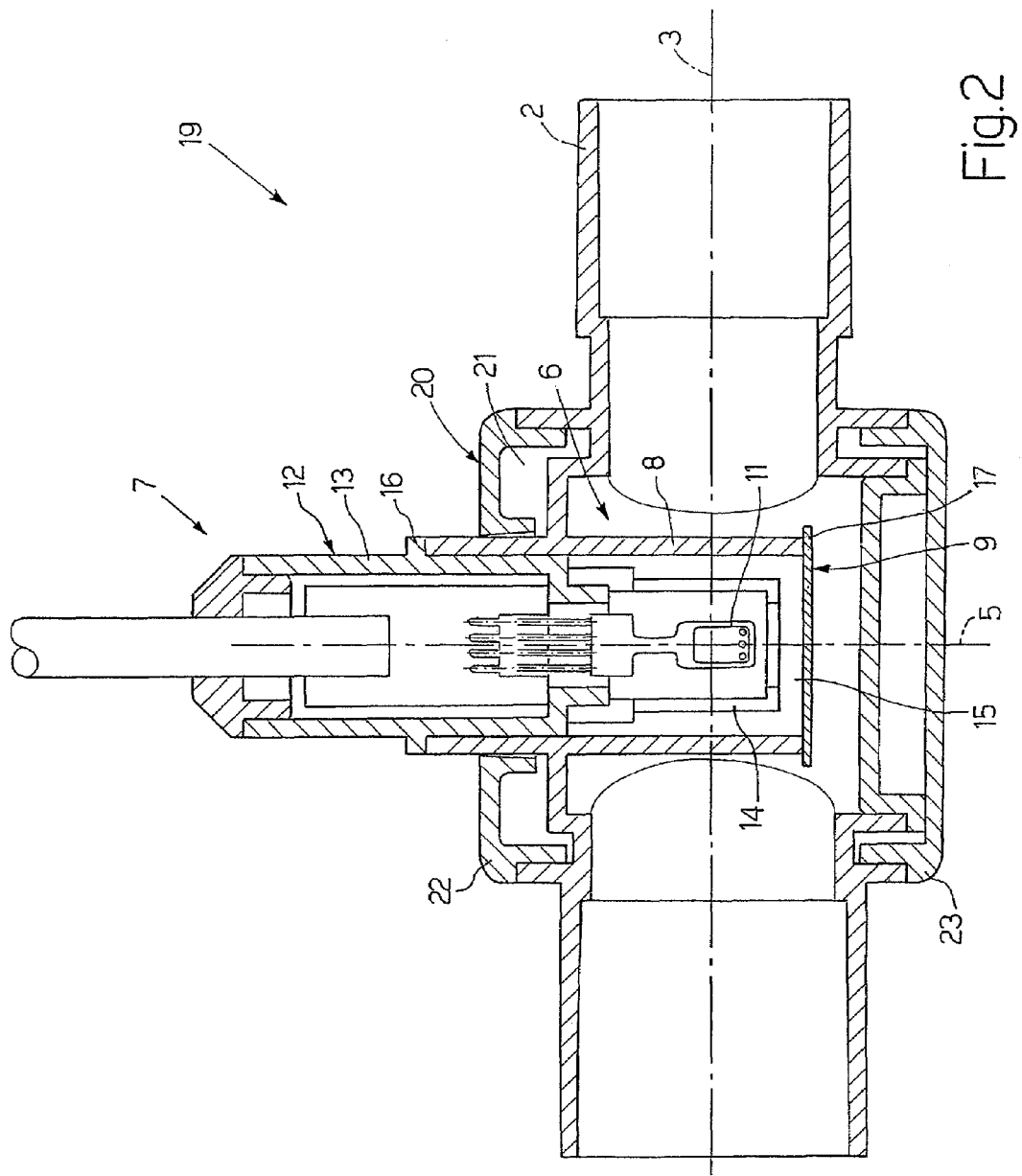
FIG. 2 shows the same view as in FIG. 1, of a variation of the FIG. 1 conduit.

The FIG. 2 variation relates to a conduit 19, which only differs from conduit 1 by receptacle 6 being formed in one piece with body 2, and by the presence of a second tubular body 20 fitted, coaxially with body 2, at receptacle 6 to define, together with body 2, an annular insulating air chamber 21 for ensuring correct operation of sensor 7.

Body 20 comprises two substantially semicylindrical shells 22, 23—of which, shell 22 is fitted through with receptacle 6—which are fitted in axially fixed manner to body 2, and are connected to each other by known fastening means not shown.

In variations not shown, diaphragm 17 may obviously define at least part of lateral wall 8 of receptacle 6. Receptacle 6 therefore has the advantage of being able to house all types of sensors 7 for controlling physical/chemical parameters of the patient's ventilation gas stream, such as temperature, pressure, humidity, and oxygen and/or carbon dioxide concentration sensors.

I claim:

1. A conduit for communicating a gas stream to a patient in a medical respiration support circuit, the conduit comprising:
    a first tubular body adapted for communicating a ventilation gas stream;
    a receptacle configured to house a sensor, the receptacle having a first end, a second end, an internal chamber, and a longitudinal axis; and
    a gas permeable filtering element proximate the first end of the receptacle to filter the flow of the gas stream into the internal chamber of the receptacle;
    wherein the second end of the receptacle is configured to receive the sensor such that the sensor may be mounted within the internal chamber of the receptacle;
    wherein the receptacle extends through an opening in the tubular body and is secured to the tubular body with a friction fit;
    wherein the receptacle includes a flange separating the first end of the hollow body from the second end of the hollow body, and wherein the flange is configured to abut the conduit when the receptacle is fully inserted through the opening in the tubular body;
    wherein the filtering element is located substantially within the conduit; and
    wherein the longitudinal axis of the receptacle is perpendicular to the gas stream flowing through the conduit.

2. The conduit of claim 1 wherein the filtering element comprises a diaphragm.

3. The conduit of claim 1, wherein the receptacle has a generally cylindrical shape.

4. The conduit of claim 1, wherein the receptacle is configured to provide a friction fit for the sensor when inserted through the second end of the receptacle.

5. The conduit of claim 1, further comprising a removable cap covering the second end of the receptacle.

6. The conduit of claim 1 further comprising a second tubular body extending about the first tubular body and the receptacle, the second tubular body defining an insulating air chamber around the receptacle.

* * * * *